US009713558B2

United States Patent
Peltier et al.

(10) Patent No.: US 9,713,558 B2
(45) Date of Patent: Jul. 25, 2017

(54) ABSORBENT ARTICLE INCLUDING LAMINATE AND METHOD OF MAKING THE SAME

(71) Applicant: 3M INNOVATIVE PROPERTIES COMPANY, St. Paul, MN (US)

(72) Inventors: Mark A. Peltier, Forest Lake, MN (US); Leigh E. Wood, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 128 days.

(21) Appl. No.: 13/679,296

(22) Filed: Nov. 16, 2012

(65) Prior Publication Data

US 2014/0142533 A1    May 22, 2014

(51) Int. Cl.
*A61F 13/62*    (2006.01)
*A61F 13/56*    (2006.01)
*A61F 13/15*    (2006.01)

(52) U.S. Cl.
CPC .... *A61F 13/5633* (2013.01); *A61F 13/15756* (2013.01); *A61F 13/622* (2013.01)

(58) Field of Classification Search
CPC .. A61F 13/62; A61F 13/622; A61F 13/15699; A61F 13/15756; A61F 13/625; A61F 13/627; A61F 13/4963; A41F 1/006; A41F 1/00; A44B 18/0069; A44B 18/0073
USPC ............ 604/391; 24/442–452; 493/393, 334
See application file for complete search history.

(56) References Cited

U.S. PATENT DOCUMENTS

| | | | |
|---|---|---|---|
| 3,848,594 A | 11/1974 | Buell | |
| 4,699,622 A | 10/1987 | Toussant et al. | |
| 4,775,310 A | 10/1988 | Fischer | |
| 4,894,060 A | 1/1990 | Nestegard | |
| 5,077,870 A | 1/1992 | Melbye et al. | |
| 5,250,253 A * | 10/1993 | Battrell | 264/557 |
| 5,462,540 A | 10/1995 | Caldwell | |
| 5,537,722 A | 7/1996 | Niederhofer et al. | |

(Continued)

FOREIGN PATENT DOCUMENTS

| | | |
|---|---|---|
| EP | 0341993 | 5/1988 |
| EP | 2255769 | 12/2010 |

(Continued)

OTHER PUBLICATIONS

US 5,389,416, Dec. 14, 1995, Mody (Withdrawn).

(Continued)

*Primary Examiner* — Peter S Vasat

(57) ABSTRACT

An absorbent article including a chassis and a laminate. The chassis has a topsheet side, a backsheet side, and first and second opposing longitudinal edges extending from a rear waist region to an opposing front waist region. The laminate includes a carrier having a first face and a second face and a fastening patch on a portion of the first face of the carrier. The laminate is wrapped around the first longitudinal edge of the chassis in the rear waist region so that the second face of the carrier contacts the topsheet side and the backsheet side of the chassis. The fastening patch includes fastening elements that are exposed on the topsheet side of the chassis. A method of making the absorbent article is also disclosed.

17 Claims, 4 Drawing Sheets

(56) References Cited

U.S. PATENT DOCUMENTS

| | | | |
|---|---|---|---|
| 5,554,146 | A | 9/1996 | Niederhofer et al. |
| 5,605,729 | A | 2/1997 | Mody et al. |
| 5,926,926 | A | 7/1999 | Kato |
| 6,075,179 | A | 6/2000 | McCormack |
| 6,190,594 | B1 | 2/2001 | Gorman et al. |
| 6,190,758 | B1 | 2/2001 | Stopper |
| 6,287,665 | B1 | 9/2001 | Hammer |
| 6,627,133 | B1 | 9/2003 | Tuma |
| 6,719,744 | B2 | 4/2004 | Kinnear et al. |
| 7,198,743 | B2 | 4/2007 | Tuma |
| 7,201,743 | B2 * | 4/2007 | Rohrl .................. 604/390 |
| 7,214,334 | B2 | 5/2007 | Jens et al. |
| 7,435,245 | B2 * | 10/2008 | Wendelstorf et al. ........ 604/391 |
| 7,438,709 | B2 | 10/2008 | Karami et al. |
| 7,658,813 | B2 * | 2/2010 | Petersen .................. 156/253 |
| 7,753,900 | B2 | 7/2010 | Ito et al. |
| 8,449,518 | B2 | 5/2013 | Allison-Rogers |
| 8,496,640 | B2 | 7/2013 | Molander |
| 8,500,711 | B2 | 8/2013 | Jackson et al. |
| 2004/0222551 | A1 * | 11/2004 | Provost .............. A44B 18/0049 264/145 |
| 2006/0027306 | A1 * | 2/2006 | Olsson .............. A61F 13/15756 156/73.1 |
| 2009/0126864 | A1 | 5/2009 | Tachibana et al. |
| 2010/0025881 | A1 | 2/2010 | Seth et al. |
| 2011/0015608 | A1 | 1/2011 | Fujioka |
| 2011/0147475 | A1 | 6/2011 | Biegler |
| 2011/0151171 | A1 | 6/2011 | Biegler et al. |
| 2011/0313389 | A1 | 12/2011 | Wood et al. |
| 2012/0204383 | A1 * | 8/2012 | Wood et al. .................. 24/306 |

FOREIGN PATENT DOCUMENTS

| | | |
|---|---|---|
| FR | 2943908 | 10/2010 |
| JP | 20000014702 | 1/2000 |
| JP | 2002-45393 | 2/2002 |
| JP | 3479395 | 12/2003 |
| JP | 2010119423 | 6/2010 |
| WO | WO 92/01401 | 2/1992 |
| WO | WO 99/53881 | 10/1999 |
| WO | WO 00/27236 | 5/2000 |
| WO | WO 00/27329 | 5/2000 |
| WO | WO 2011-163020 | 12/2011 |
| WO | WO 2012/009687 | 1/2012 |
| WO | WO 2012-154659 | 11/2012 |

OTHER PUBLICATIONS

International Search Report for PCT International Application No. PCT/US2013/070385, mailed Feb. 11, 2014, 3 pages.

Communication and Supplementary European Search Report, European Patent Application 13854829.2, May 31, 2016, 4 pages.

* cited by examiner

ABSORBENT ARTICLE INCLUDING LAMINATE AND METHOD OF MAKING THE SAME

BACKGROUND

Mechanical fasteners, which are also called hook and loop fasteners, are useful for providing releasable attachment in numerous applications. For example, mechanical fasteners are widely used in wearable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Absorbent articles often employ woven or nonwoven materials, for example, to provide a cloth-like feeling in order to increase the comfort of wearing.

Fastening tabs often have a manufacturer's end that is attached to the rear waist region of an absorbent article and a user's end that can be grasped and extends outwardly beyond the edge of an absorbent article before it is attached to the front waist region of the absorbent article. The attachment point of the tab at the manufacturer's end must be strong enough to withstand the force applied during the application and wearing of the absorbent article; otherwise the tab can separate from the absorbent article during use. So called Y-bonded fastening tabs are proposed to have strong attachment to absorbent articles; see, e.g., U.S. Pat. No. 3,848,594 (Buell).

In some cases, fastening tabs include a substrate that is coated entirely with adhesive. The adhesive at the manufacturer's end is used to permanently attach the fastening tab to the edge of the absorbent article, and the adhesive at the user's end is used to attach the hook strip or patch to the fastening tab. Exposed adhesive between the edge of the absorbent article and the hook strip or patch can be managed by means of a release tape, for example, on a surface of the absorbent article that comes into contact with the exposed adhesive while the absorbent article is in the package.

SUMMARY

The present disclosure provides an absorbent article including a chassis and a laminate wrapped around an edge of the chassis. Advantageously, the laminate can readily be attached firmly to the chassis, can strengthen at least a portion of the edge of the chassis, can avoid problems with flagging, and can advantageously be used in the absence of release tape.

In one aspect, the present disclosure provides an absorbent article including a chassis and a laminate. The chassis has a topsheet side, a backsheet side, and first and second opposing longitudinal edges extending from a rear waist region to an opposing front waist region. The laminate includes a carrier having a first face and a second face and a fastening patch on a portion of the first face of the carrier. The laminate is wrapped around the first longitudinal edge of the chassis in the rear waist region so that the second face of the carrier contacts the topsheet side and the backsheet side of the chassis. The fastening patch includes fastening elements that are exposed on the topsheet side of the chassis.

In another aspect, the present disclosure provides a method of making an absorbent article. The method includes providing a chassis and a laminate, wrapping the laminate around the first longitudinal edge of the chassis in the rear waist region, and attaching the laminate to the chassis. The chassis has a topsheet side, a backsheet side, and first and second opposing longitudinal edges extending from a rear waist region to an opposing front waist region. The laminate includes a carrier having a first face and a second face and a fastening patch on a portion of the first face of the carrier. Wrapping the laminate around the chassis is carried out so that the second face of the carrier contacts the topsheet side and the backsheet side of the chassis with the fastening patch positioned so that fastening elements are exposed on the topsheet side of the chassis. In some embodiments, the laminate is provided from a roll of a carrier web having a first face and a second face and a fastening strip on the first face of the carrier web.

In this application:

Terms such as "a", "an" and "the" are not intended to refer to only a singular entity, but include the general class of which a specific example may be used for illustration. The terms "a", "an", and "the" are used interchangeably with the term "at least one".

The phrase "comprises at least one of" followed by a list refers to comprising any one of the items in the list and any combination of two or more items in the list. The phrase "at least one of" followed by a list refers to any one of the items in the list or any combination of two or more items in the list.

The term "machine direction" (MD) as used herein denotes the direction of a running, continuous web during the manufacturing of the absorbent article disclosed herein. In a roll, for example, comprising a carrier web and a fastening strip, the machine direction corresponds to the longitudinal direction of the roll. Accordingly, the terms machine direction and longitudinal direction may be used herein interchangeably. The term "cross-direction" (CD) as used herein denotes the direction that is essentially perpendicular to the machine direction. When a portion of the laminate disclosed herein is cut from a roll, the cross-direction corresponds to the width of the roll.

The terms "first", "second", and "third" are used in this disclosure. It will be understood that, unless otherwise noted, those terms are used in their relative sense only. For these components, the designation of "first", "second", and "third" may be applied to the components merely as a matter of convenience in the description of one or more of the embodiments.

All numerical ranges are inclusive of their endpoints and nonintegral values between the endpoints unless otherwise stated.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
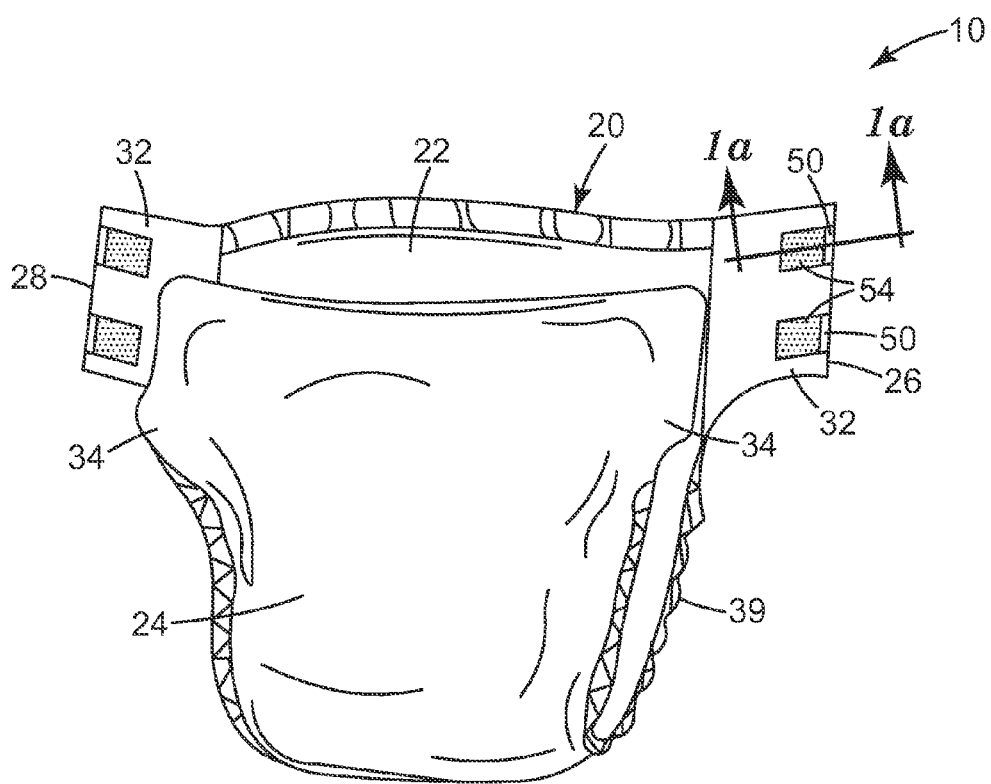
FIG. 1 is a schematic, perspective view of one embodiment of an absorbent article according to the present disclosure and/or made according to a method of the present disclosure.

Absorbent articles according to the present disclosure include diapers and adult incontinence articles, for example. A schematic, perspective view of one embodiment of an absorbent article 10 according to the present disclosure and/or made according to a method of the present disclosure is shown in FIG. 1. Absorbent article 10 includes a chassis 20 with a topsheet side 22 and a backsheet side 24. The chassis 20 also has first and second opposing longitudinal edges 26 and 28 extending from a rear waist region 32 to an opposing front waist region 34. The longitudinal direction of the absorbent article 10 refers to the direction extending between the rear waist region 32 and the front waist region 34. Therefore, the term "longitudinal" refers to the length of the absorbent article 10, for example, when it is in an open configuration.

At least one of the front waist region 34 or the rear waist region 32, more typically the rear waist region 32, comprises at least one laminate 50. The laminate 50 includes a carrier 52 having a first face and a second face, which is shown more clearly in the cross-section shown in FIG. 1a, and a fastening patch 54 on a portion of the first face of the carrier 52. The laminate 50 is wrapped around the first longitudinal edge 26 of the chassis 20 in the rear waist region 32 so that the second face of the carrier 50 contacts both the topsheet side 22 and the backsheet side 24 of the chassis 20. The fastening patch 54 is positioned so that fastening elements 55 are exposed on the topsheet 22 side of the chassis 20. The fastening patch 54 does not extend beyond the first longitudinal edge 26 of the chassis 20. However, in some embodiments, the fastening patch does extend beyond the first longitudinal edge 26 of the chassis 20.

In absorbent articles according to the present disclosure and/or made according to the method of the present disclosure, the topsheet is typically permeable to liquid and designed to contact a wearer's skin, and the outwardly facing backsheet is typically impermeable to liquids. There is typically an absorbent core encased between the topsheet and the backsheet. Various materials can be useful for the topsheet, the backsheet, and the absorbent core in an absorbent article according to the present disclosure. Examples of materials useful for topsheets include apertured plastic films, woven fabrics, nonwoven webs, porous foams, and reticulated foams. In some embodiments, the topsheet is a nonwoven material. Examples of suitable nonwoven materials include spunbond or meltblown webs of fiber forming polymer filaments (e.g., polyolefin, polyester, or polyamide filaments) and bonded carded webs of natural polymers (e.g., rayon or cotton fibers) and/or synthetic polymers (e.g., polypropylene or polyester fibers). The nonwoven web can be surface treated with a surfactant or otherwise processed to impart the desired level of wettability and hydrophilicity. The backsheet is sometimes referred to as the outer cover and is the farthest layer from the user. The backsheet functions to prevent body exudates contained in absorbent core from wetting or soiling the wearer's clothing, bedding, or other materials contacting the diaper. The backsheet can be a thermoplastic film (e.g., a poly(ethylene) film). The thermoplastic film may be embossed and/or matte finished to provide a more aesthetically pleasing appearance. The backsheet can also include woven or nonwoven fibrous webs, for example, laminated to the thermoplastic films or constructed or treated to impart a desired level of liquid impermeability even in the absence of a thermoplastic film. Suitable backsheets also include vapor or gas permeable microporous "breathable" materials that are substantially impermeable to liquid. Suitable absorbent cores include natural, synthetic, or modified natural polymers that can absorb and hold liquids (e.g., aqueous liquids). Such polymers can be crosslinked (e.g., by physical entanglement, crystalline domains, covalent bonds, ionic complexes and associations, hydrophilic associations such as hydrogen bonding, and hydrophobic associations or Van der Waals forces) to render them water insoluble but swellable. Such absorbent materials are usually designed to quickly absorb liquids and hold them, usually without release. Examples of suitable absorbent materials useful in absorbent articles disclosed herein include wood pulp or other cellulosic materials and super absorbent polymers (SAP).

In some embodiments of the absorbent article and method disclosed herein, including the embodiment illustrated in FIG. 1, the absorbent article 10 has ear portions in the rear waist region 32 to which the laminates 50 are attached. For the purposes of the present disclosure, the ear portions are considered part of the chassis 20. Absorbent articles (e.g., incontinence articles and diapers) according to the present disclosure may have any desired shape such as a rectangular shape, a shape like the letter I, a shape like the letter T, or an hourglass shape. The absorbent article may also be a refastenable pants-style diaper with laminates 50 along each longitudinal edge. In some embodiments, including the embodiment shown in FIG. 1a, the topsheet and backsheet are attached to each other and together form chassis 20 all the way out to the first and second longitudinal opposing edges 26 and 28. That is, the topsheet and backsheet together form the ears shown in FIGS. 1 and 1a. In some embodiments, only one of the topsheet or the backsheet extends to the first and second longitudinal opposing edges 26 and 28. In other embodiments, the chassis can include separate side panels that are attached to the sandwich of at least topsheet, backsheet, and absorbent core during manufacturing of the absorbent article, for example, to form ear portions. The side panels can be made of a material that is the same as the topsheet or backsheet or may be made from a different material (e.g., a different nonwoven). In these embodiments, the side panels also form part of the chassis. In any of these embodiments, the absorbent article may comprise an elastic material 39 along at least a portion of first and second longitudinal side edges 26 and 28 to provide leg cuffs.

In the embodiment illustrated in FIG. 1, there are two of the laminates 50 wrapped around the first longitudinal edge 26 of the chassis 20 in the rear waist region 32 and two of the laminates 50 wrapped around the second longitudinal edge 28 of the chassis 20 in the rear waist region 32. Providing two laminates on each of the first and second longitudinal edges 26 and 28 may be advantageous if the absorbent article 10 is relatively large in size (e.g., in an adult incontinence article) although this is not a requirement. In some embodiments not illustrated, there is one laminate 50 wrapped around the first longitudinal edge 26 of the chassis 20 in the rear waist region 32 and one laminate 50 wrapped around the second longitudinal edge 28 of the chassis 20 in the rear waist region 32.

Figure 1A:
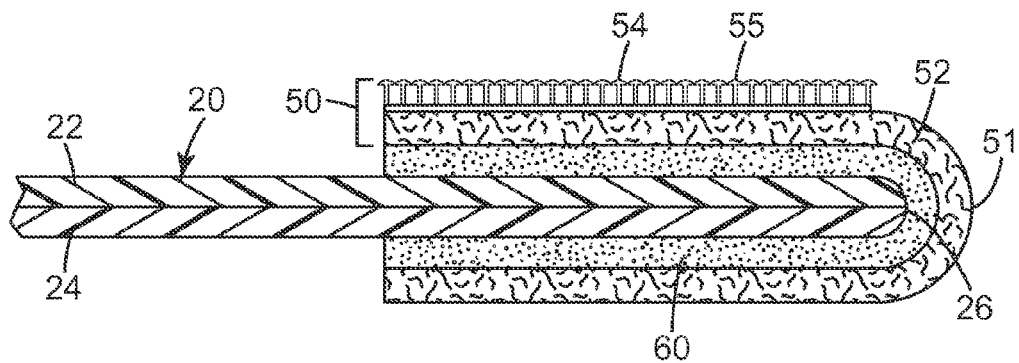
FIG. 1a is an example of a cross-section taken through line 1a-1a in FIG. 1.
Figure 1B:
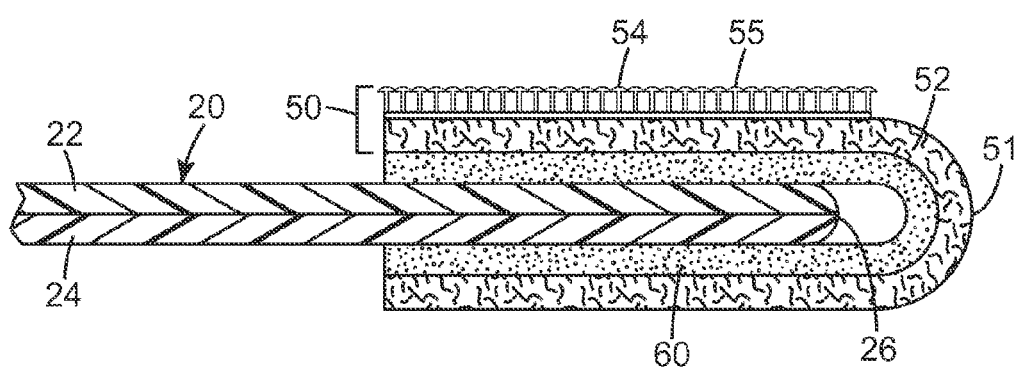
FIG. 1b is another example of a cross-section of a laminate wrapped around a longitudinal edge of an absorbent article according to the present disclosure and/or made according to a method of the present disclosure.

Wrapping the laminate around the longitudinal edge of the chassis creates a fold in the laminate. The fold refers to a position where the laminate is turned back so that two portions of the laminate lie alongside each other along opposite sides of the chassis. However, the fold is not required to be creased. In some embodiments of the absorbent article and method disclosed herein, including the embodiment illustrated in FIGS. 1 and 1a, the laminate 50 is wrapped around the chassis 20 so that the fold 51 is flush with the first longitudinal edge 26 of the chassis 20. Although this configuration is advantageous for reasons described in further detail, below, it is not a requirement. There may be space between the edge 26 of the chassis 20 and the fold 51 of the laminate 50 as shown in FIG. 1b. For example, the fold 51 of the laminate 50 may be within 5 (in some embodiments, 4, 3, 2, or 1) millimeters of the edge 26 of the chassis 20. Also, the fold 51 of the laminate may be at an angle to the edge of the chassis 20 (e.g., up to a 45, 30, 20, or 10 degree angle.)

Figure 2:
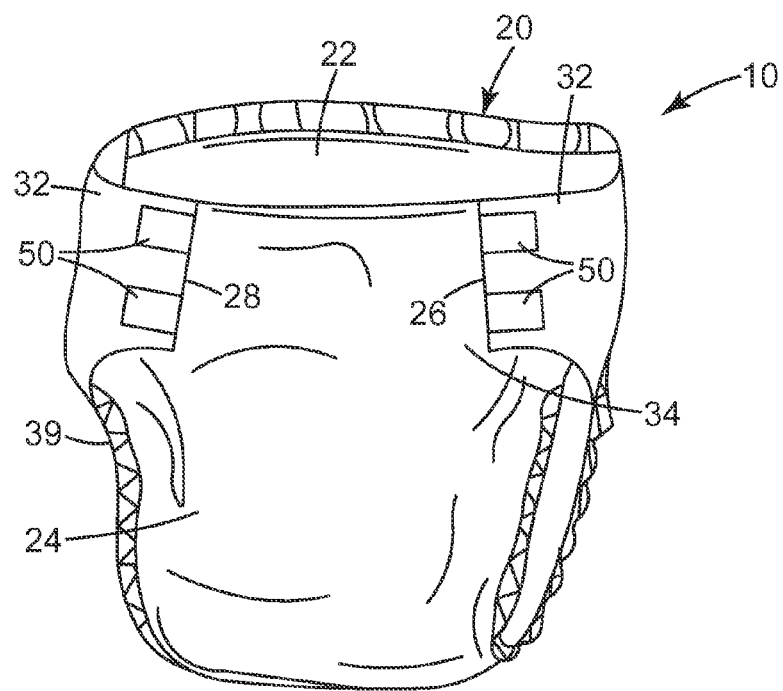
FIG. 2 is a perspective view of the absorbent article shown in FIG. 1, which shows how the absorbent article may be fastened around a person's waist.

When the absorbent article shown 10 in FIG. 1 is worn, the rear waist region 32 may be wrapped around the wearer's body to overlap and engage with the front waist region 34 as shown in FIG. 2. In this configuration, the fastening patches 54 of the laminates 50 face the backsheet and so are not visible in FIG. 2. In some embodiments, the fastening patches 54 can be engage with a target area (not shown) comprising a fibrous material arranged on the backsheet of the front waist region 34. For example, loop tapes such as those disclosed in U.S. Pat. No. 5,389,416 (Mody et al.) EP 0,341,993 (Gorman et al.) and EP 0,539,504 (Becker et al.) may be applied to a target area to provide an exposed fibrous material. In other embodiments, the backsheet comprises a woven or nonwoven fibrous layer which is capable of interacting with the fastening patch 54. Examples of such backsheets 24 are disclosed, for example, in U.S. Pat. No. 6,190,758 (Stopper) and U.S. Pat. No. 6,075,179 (McCormack et al.). In these embodiments, the fastening patches 54 of the laminates 50 advantageously may engage with any suitable location on the backsheet, which can be determined by the size of the wearer and the desired fit.

Figure 3:
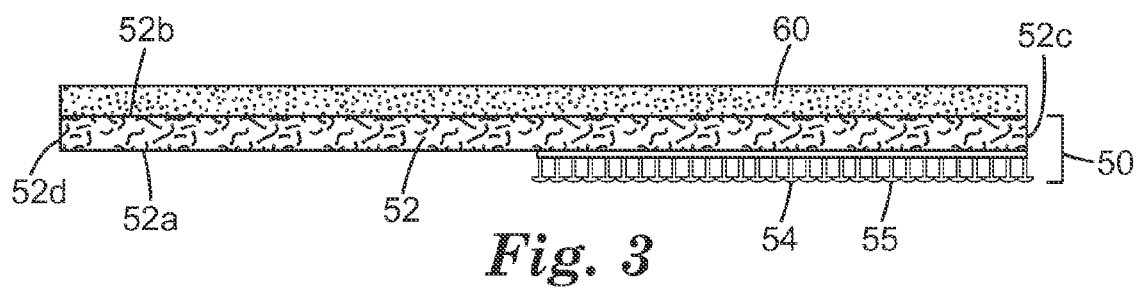
FIG. 3 is a side view of one embodiment of a laminate included in an absorbent article according to the present disclosure.

Referring now to FIG. 3, laminate 50 includes a carrier 52 having a first face 52a and a second face 52b. To a portion of the first face 52a of the carrier 52 is attached a fastening patch 54. In the illustrated embodiment, the second face 52b of the carrier 52 is provided with a layer of adhesive 60. The carrier 52 may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, paper, plastic films (e.g., single- or multi-layered films, coextruded films, laterally laminated films, or films comprising foam layers), and combinations thereof. Any of these materials can be selected to be flexible enough to allow the carrier to be folded over the first longitudinal edge of the chassis. In some embodiments, the carrier is a fibrous material (e.g., a woven, nonwoven, or knit material). In some embodiments, the carrier comprises a nonwoven. The term "nonwoven" when referring to a carrier or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes. In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer (e.g., a thermoplastic film layer).

Fibrous materials that can provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material. In some embodiments, one or more zones of the carrier may comprise one or more elastically extensible materials extending in at least one direction when a force is applied and returning to approximately their original dimension after the force is removed. However, in some embodiments, at least the portion of the carrier joined to the fastening patch is not stretchable or has up to a 10 (in some embodiments, up to 9, 8, 7, 6, or 5) percent elongation in the CD. In some embodiments, the carrier may be extensible but nonelastic. In other words, the carrier may have an elongation of at least 5, 10, 15, 20, 25, 30, 40, or 50 percent but substantially no recovery from the elongation (e.g., up to 10 or 5 percent recovery). Suitable extensible carriers may include nonwovens (e.g., spunbond, spunbond meltblown spunbond, or carded nonwovens). In some embodiments, the nonwoven may be a high elongation carded nonwoven (e.g., HEC).

Useful carriers may have any suitable basis weight or thickness that is desired for a particular application. For a fibrous carrier, the basis weight may range, e.g., from at least about 5, 8, 10, 20, 30, or 40 grams per square meter, up to about 400, 200, 100, or 50 grams per square meter. The carrier may be up to about 5 mm, about 2 mm, or about 1 mm in thickness and/or at least about 0.1, about 0.2, or about 0.5 mm in thickness.

Referring again to FIG. 3, the fastening patch 54 on a portion of the first face 52a of the carrier 52 typically has upstanding male fastening elements 55 on a backing. The backing and the male fastening elements 55 are typically integral (that is, formed at the same time as a unit, unitary). Fastening patches are typically made from at least one thermoplastic material. Suitable thermoplastic materials for mechanical fasteners include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the thermoplastic is a polyolefin (e.g., polyethylene, polypropylene, polybutylene, ethylene copolymers, propylene copolymers, butylene copolymers, and copolymers and blends of these materials).

Upstanding male fastening elements on a backing can be made, for example, by feeding a thermoplastic material onto a continuously moving mold surface with cavities having the inverse shape of the posts. The thermoplastic material can be passed between a nip formed by two rolls or a nip between a die face and roll surface, with at least one of the rolls having the cavities. The cavities may be in the inverse shape of a capped post having a loop-engaging head or may be in the inverse shape of a post without loop-engaging heads (e.g., a precursor to a male fastening element). Pressure provided by the nip forces the resin into the cavities. In some embodiments, a vacuum can be used to evacuate the cavities for easier filling of the cavities. The nip typically has a large enough gap such that a coherent backing is formed over the cavities. The mold surface and cavities can optionally be air or water cooled before stripping the integrally formed backing and upstanding hook elements from the mold surface such as by a stripper roll. If the posts formed upon exiting the cavities do not have loop-engaging heads, loop-engaging heads could be subsequently formed into hooks by a capping method as described in U.S. Pat. No. 5,077,870 (Melbye et al.). Typically, the capping method includes deforming the tip portions of the hook elements using heat and/or pressure. The heat and pressure, if both are used, could be applied sequentially or simultaneously.

Suitable tool rolls include those formed from a series of plates defining a plurality of post-forming cavities about its periphery such as those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another exemplary method for forming a thermoplastic backing with upstanding posts includes using a flexible mold belt defining an array of upstanding post-shaped cavities as described in U.S. Pat. No. 7,214,334 (Jens et al.). Yet other useful methods for forming a thermoplastic backing with upstanding posts can be found in U.S. Pat. No. 6,287,665 (Hammer), U.S. Pat. No. 7,198,743 (Tuma), and U.S. Pat. No. 6,627,133 (Tuma).

Another method for forming a thermoplastic backing with upstanding male fastening elements is profile extrusion, which is described, for example, in U.S. Pat. No. 4,894,060 (Nestegard). Typically, in this method a thermoplastic flow stream is passed through a patterned die lip (e.g., cut by electron discharge machining) to form a web having down-web ridges. The ridges can then be transversely sliced at spaced locations along the extension of the ridges to form upstanding fastening elements with a small separation caused by the cutting blade. The separation between upstanding fastening elements is then increased by stretching.

The male fastening elements on the fastening patch of the laminate typically have loop-engaging heads that have an overhang. The term "loop-engaging" as used herein relates to the ability of a male fastening element to be mechanically attached to a loop material. Suitable male fastening elements with loop-engaging heads can have any desired shape. For example, the male fastening element may be in the shape of a mushroom (e.g., with a circular or oval head enlarged with respect to the stem), a hook, a palm-tree, a nail, a T, or a J. The loop-engageability of male fastening elements may be determined and defined by using standard woven, nonwoven, or knit materials. A region of male fastening elements with loop-engaging heads generally will provide, in combination with a loop material, at least one of a higher peel strength, higher dynamic shear strength, or higher dynamic friction than a region of posts without loop-engaging heads. Typically, male fastening elements that have loop-engaging heads have a maximum thickness dimension (in either dimension normal to the height) of up to about 1 (in some embodiments, 0.9, 0.8, 0.7, 0.6, 0.5, or 0.45) millimeter.

The male fastening elements on the fastening patch of the laminate can have a variety of useful maximum heights (above the backing) of up to 3 mm, 1.5 mm, 1 mm, or 0.5 mm and, in some embodiments a minimum height of at least 0.05 mm, 0.1 mm, or 0.2 mm. The upstanding posts have a variety of aspect ratios (that is, a ratio of height to width at the widest point) such as at least about 2:1, 3:1, or 4:1. Advantageously, a variety of densities of the upstanding fastening elements may be useful. For example, the male fastening elements have a density of at least 248 per square centimeter ($cm^2$) (1600 per square inch, $in^2$) and up to about 1500/$cm^2$ (10000/$in^2$), 1240/$cm^2$ (8000/$in^2$), or 852/$cm^2$ (5500/$in^2$). For example, the density of the male fastening elements may be in a range from 271/$cm^2$ (1750/$in^2$) to about 852/$cm^2$ (5500/$in^2$) or from 248/$cm^2$ (1600/$in^2$) to 542/$cm^2$ (3500/$in^2$). The spacing of the male fastening elements need not be uniform.

For laminates included in the absorbent articles according to the present disclosure and/or made according to the method of the present disclosure, the fastening patch 54 is on a portion of the first face of the carrier 52 as shown, for example, in FIG. 3. The fastening patch 54 may be joined to the carrier 52, for example, by lamination (e.g., extrusion lamination), adhesives (e.g., pressure sensitive adhesives, hot melt adhesives, or structural adhesives), or other bonding methods (e.g., ultrasonic bonding, thermal bonding, compression bonding, or surface bonding).

In some embodiments the fastening patch is joined to the carrier using surface bonding or loft-retaining bonding techniques. The term "surface-bonded" when referring to the bonding of fibrous materials means that parts of fiber surfaces of at least portions of fibers are melt-bonded to the backing of the fastening patch, on a side opposite the male fastening elements, in such a manner as to substantially preserve the original (pre-bonded) shape of the surface of the backing and to substantially preserve at least some portions of the surface of the backing in an exposed condition in the surface-bonded area. Quantitatively, surface-bonded fibers may be distinguished from embedded fibers in that at least about 65% of the surface area of the surface-bonded fiber is visible above the surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded. In some of these embodiments, joining the fastening patch to a fibrous carrier comprises impinging heated gaseous fluid (e.g., ambient air, dehumidified air, nitrogen, an inert gas, or other gas mixture) onto a first surface of the fibrous web carrier while it is moving; impinging heated fluid onto the second surface of the backing while the continuous web is moving, wherein the second surface is opposite the male fastening elements; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. Further methods and apparatus for joining a continuous web to a fibrous carrier web using heated gaseous fluid may be found in U.S. Pat. Appl. Pub. Nos. 2011/0151171 (Biegler et al.) and 2011/0147475 (Biegler et al.).

Figure 4A:
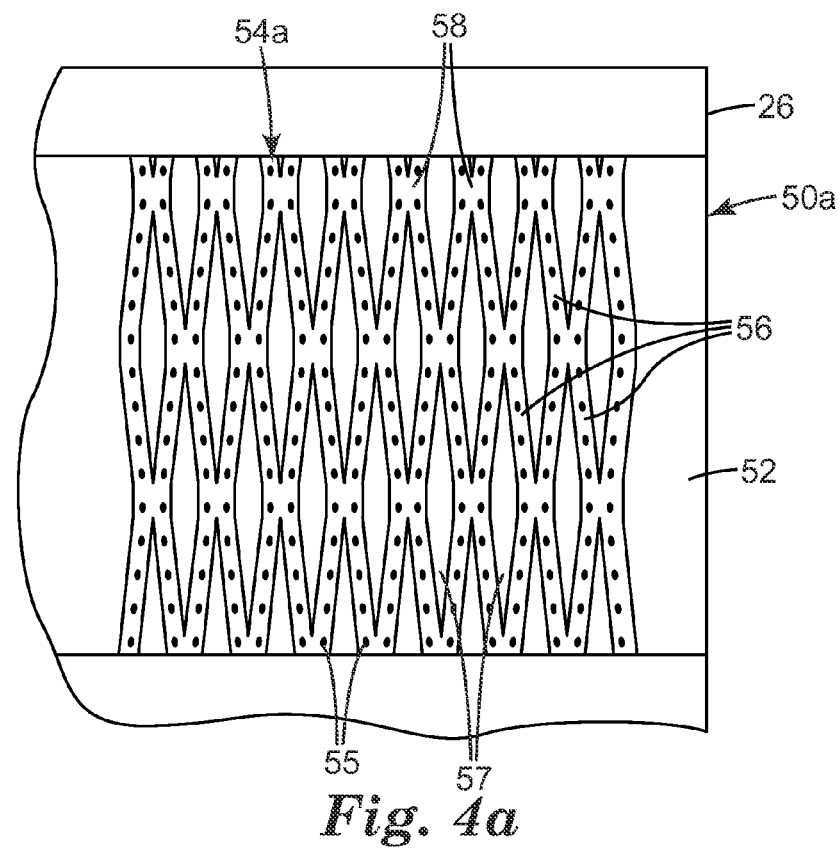
FIG. 4a is a schematic, top view of an edge of another embodiment of an absorbent article according to the present disclosure and/or made according to the method of the present disclosure.

For any of the embodiments of the absorbent article according to the present disclosure or the method of making an absorbent article according to the present disclosure, including embodiments which incorporate a laminate as shown in FIG. 4a, the fastening patch may include openings 57. FIG. 4a illustrates an expanded view of laminate 50a wrapped around the first longitudinal edge 26 of an absorbent article. The openings 57 in fastening patch 54a may be in the form of a repeating pattern of geometric shapes such as polygons. The polygons may be, for example, hexagons or quadrilaterals such as parallelograms or diamonds. The openings 57 may be formed in the fastening patch 54a by any suitable method, including die punching. In some embodiments, the openings may be formed by slitting the thermoplastic backing of a fastening patch 54a to form multiple strands 56 attached to each other at intact bridging regions 58 in the backing and separating at least some of the multiple strands 56 between at least some of the bridging regions 58. The bridging regions 58 are regions where the backing is not cut through, and at least a portion of the bridging regions can be considered collinear with the slits. The intact bridging regions 58 of the backing serve to divide the slits into a series of spaced-apart slit portions aligned in the direction of slitting (e.g., the machine direction), which can be referred to as interrupted slits. In some embodiments, for at least some adjacent interrupted slits, the spaced-apart slit portions are staggered in a direction transverse to the slitting direction (e.g., the cross-machine direction). The interrupted slits may be cut into the backing between some pairs of adjacent rows of male fastening elements 55 although this is not a requirement. In some embodiments, curved lines may be used, which can result in crescent shaped openings after spreading. There may be more than one repeating pattern of geometric shaped openings. The openings may be evenly spaced or unevenly spaced as desired. For openings that are evenly spaced, the spacing between the openings may differ by up to 10, 5, 2.5, or 1 percent. Further details about providing openings in a mechanical fastener can be found in U.S. Appl. Pub. No. 2012/0204383 (Wood et al.). In some embodiments, the fastening patch can comprise multiple strands 56 attached to each other at intact bridging regions 58 in the backing without spreading the strands apart to create openings. The interrupted slits may be made in either the longitudinal direction of the absorbent article or in a transverse direction. Such slits may improve the flexibility of the fastening patch improve the peel performance. Further details about providing interrupted slits in a mechanical fastener can be found in U.S. Appl. Pub. No. 2011/0313389 (Wood et al.).

Figure 4B:
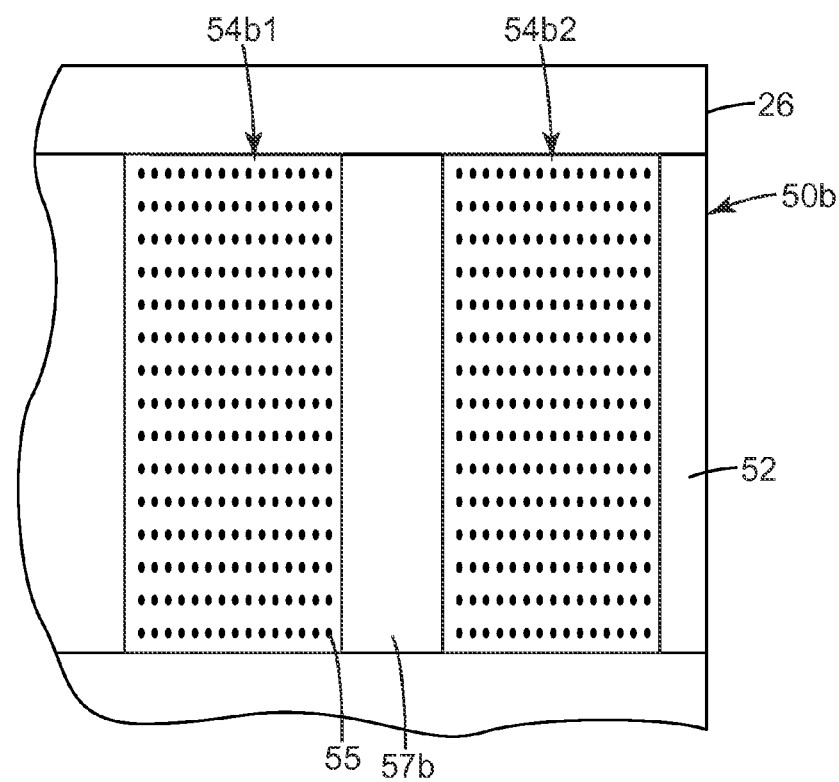
FIG. 4b is a schematic, top view of an edge of still another embodiment of an absorbent article according to the present disclosure and/or made according to the method of the present disclosure.

The laminate can include more than one fastening patch. In some embodiments, the laminate comprises a second fastening patch on a second portion of the first face of the carrier. FIG. 4b illustrates an expanded view of laminate 50b wrapped around the first longitudinal edge 26 of an absorbent article. The second fastening patch 54b2 and the first fastening patch 54b1 may be abutting, or they may be separated by a distance 57b that is usually smaller than the length of each fastening patch (that is, in the direction of the longest dimension of the carrier 52). The first and second fastening patches 54b1, 54b2 may be the same or different sizes in either the length or width dimension. An example of a suitable configuration of two fastening patches is described in Int. Pat. Appl. Pub. No. WO 2011/163020 (Hauschildt et al.).

In some embodiments wherein the fastening patch includes openings 57 (e.g., diamond- or hexagonal-shaped openings), including the embodiment illustrated in FIG. 4a, the carrier 52 does not include openings. In some embodiments, the fastening patch 54a is bonded to the carrier 52 with adhesive to form the laminate 50a, and the adhesive is exposed in the openings 57. In some embodiments, the adhesive is a pressure sensitive adhesive. However, in other embodiments, pressure sensitive adhesive is not exposed in the openings.

In any of the embodiments of the laminate 50 included in the absorbent article according to the present disclosure or made by a method according to the present disclosure, the fastening patch 54 is located on a portion on the first face of the carrier 52. The portion can include any part of the carrier other than the whole. The portion may include the edge 52c of the carrier 52 as shown in FIG. 3. Or the fastening patch may be displaced from the edge of the carrier as shown in FIG. 4a. The fastening patch is typically positioned closer to one end of the carrier 52c than the other 52d as shown in FIG. 3, and the end 52d of the carrier opposite to the end 52c including the fastening patch is wrapped around the edge of the chassis so it is on the opposite side of the chassis as the fastening patch as shown in FIG. 2. The fastening patch may have a length that is up to ⅘ or ⅔ the length of the carrier, which is the longest dimension of the carrier. The fastening patch may have a length that is at least ¼ or ⅓ the length of the carrier. In the width direction, the fastening patch may be the same size as the carrier, or the fastening patch may be smaller in width than the carrier. In some embodiments, the width of the fastening patch is at least ½ or ¾ the width of the carrier.

The size of the carrier and of the laminate may be such that it is suitable for the desired size of the absorbent article. In some embodiments, for example, when the laminate is useful for an adult incontinence article, the carrier has a length in a range from 50 millimeters to 80 millimeters and a width in a range from 15 millimeters to 40 millimeters. In some of these embodiments, the carrier has a length in a range from 55 millimeters to 70 millimeters and a width in a range from 25 millimeters to 30 millimeters. In some embodiments, when the laminate is useful for a baby diaper, the carrier has a length in a range from 25 millimeters to 60 millimeters and a width in a range from 10 millimeters to 30 millimeters.

In the absorbent article according to the present disclosure and/or made according to the method of the present disclosure, the laminate is attached to the chassis. Referring again to FIG. 1a, the laminate 50 may be attached to the chassis 20 using any suitable method. For example, adhesives (e.g., pressure sensitive adhesives, hot melt adhesives, or structural adhesives), non-adhesive bonding (e.g., ultrasonic bonding, thermal bonding, compression bonding, or surface bonding as described above), or a combination of any of these methods may be useful. In FIG. 1a, the laminate 50 is attached to the chassis 20 using adhesive 60.

For the method of making an absorbent article according to the present disclosure, conveniently, it may be useful to provide a continuous web of a plurality of chassis including the absorbent core encased between the topsheet and the backsheet. The chassis in the continuous web may have any shape or construction as described above in connection with FIG. 1. In some embodiments, the laminate is also provided as a continuous web. For example, the laminate can be provided from a roll of a carrier web having a first face and a second face and a fastening strip on the first face of the carrier web. The carrier web and the fastening strip can be made from any of the materials described above for the carrier and the fastening patch, respectively. The roll can be unwound to provide a plurality of the laminates. In some embodiments, the roll includes perforations through the thickness of the fastening strip and the carrier web or other lines of weakness (e.g., partial-depth cut or thinned portion of the carrier web and/or fastening strip) that allows a plurality of individual laminates to be separated from the roll. Such lines of weakness may be in the cross-direction of the roll. In other embodiments, the method further includes slitting the roll after unwinding to provide a plurality of the laminates.

Figure 5A:
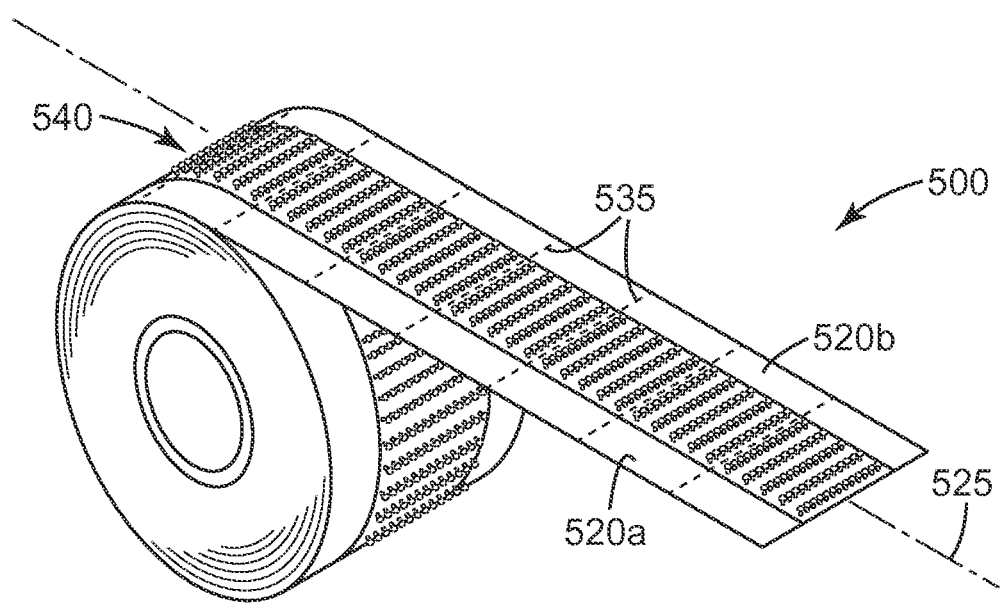
FIG. 5a is a perspective view of a roll useful for making an absorbent article according to the method of the present disclosure.
Figure 5B:
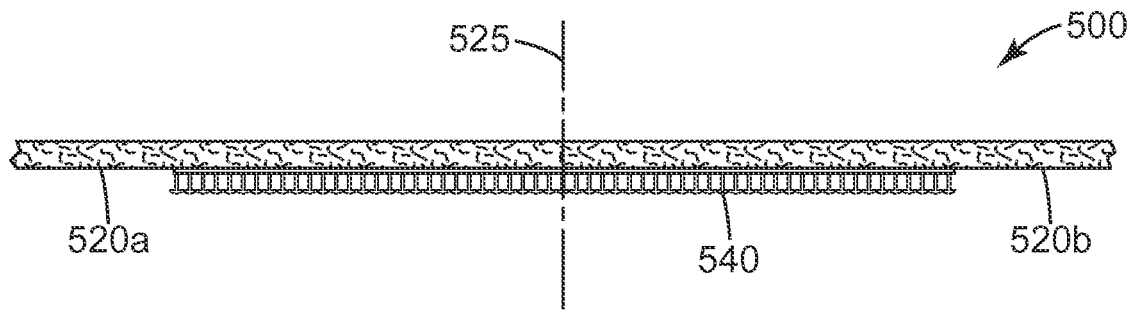
FIG. 5b is a side view of an embodiment of a laminate useful for making an absorbent article according to the method of the present disclosure.

In some embodiments, the roll or continuous web useful for providing the laminate includes a fastening strip provided in a central portion of the carrier web such that the first face of the carrier web is exposed on each side of the fastening strip. An example of such a roll is shown in FIG. 5a. A cross-section or side view of such a roll is shown in FIG. 5b. Fastening strip 540 is shown in the central portion of laminate roll 500. The carrier web is exposed at 520a and 520b on either side of the fastening strip 540. In addition to lines of weakness 535 in the cross-direction as described above, which may allow individual laminates to be separated from the roll, laminate roll 500 can include a line of weakness represented by line 525 in the center portion of the roll. Thus, laminate roll 500 may be considered a "two-up" roll. Laminates for attachment along both the first and second opposing longitudinal edges of the chassis can be provided from the same laminate roll 500 in this embodiment. Other configurations of "two-up" rolls are also possible.

In many embodiments, the roll or continuous web useful for providing the laminate does not include exposed adhesive. The roll can therefore be stable for storage wound in a level or planetary fashion. FIG. 5a illustrates a planetary-wound roll. A continuous web of the laminates can also be festooned, if desired.

Advantageously, laminates useful for the absorbent articles according to the present disclosure can be handled with conventional diaper- or incontinence article-manufacturing equipment. For example, the laminates are provided and fed to a continuous web of a plurality of chassis by one or more vacuum wheel applicators. A laminate roll can be cut with a pinch cut knife and anvil. Also, a paddle wheel apparatus can be used where a laminate roll is extruded through a window knife and shear cut by a rotating fly knife. Conventional manufacturing equipment for absorbent articles further includes glue-in-line capability as well as ultrasonic or thermal bonding equipment, any of which may be useful, alone or in combination, to attach the laminate to the chassis. At the manufacturing site for the absorbent article adhesive 60 can be applied to the second face of the carrier 52 as shown in FIG. 3, and the laminate can then be wrapped around and attached to the first longitudinal edge of the chassis. Although the adhesive 60 is shown to extend to the ends 52c and 52d of the carrier 52, this is not a requirement. It may be advantageous to coat the adhesive 60 on the carrier 52 so that the adhesive 60 does not extend all the way to the ends 52a and 52b to avoid any exposed adhesive in the absorbent article.

In other embodiments of the method of making an absorbent article disclosed herein, the laminate may be provided, either in roll form or in individual laminate form, with adhesive coated on the second face 52b of the carrier 52. In these embodiments, the laminate may include a release liner, which may be removed for attaching the laminate to the chassis. In this embodiments also, the adhesive need not extend to the ends 52c and 52d of the carrier.

Absorbent articles according to and/or made according to the method of the present disclosure have several advantages over absorbent articles having fastening tabs with a fastening patch that is located outboard of the longitudinal edge of the chassis of the absorbent article. For example, in embodiments in which the fold of the laminate is flush with the longitudinal edge of the chassis or within 5 (in some embodiments, 4, 3, 2, or 1) millimeters of the edge of the chassis 20, the absorbent article according to the present disclosure does not have the problems with flagging that can occur with absorbent articles having fastening tabs that can open during manufacturing or packaging. Also, the absorbent articles described herein typically do not require a release tape since, in most embodiments, there is not exposed adhesive on the carrier. Eliminating release tape can reduce cost in the absorbent article and reduce the stiffness in the waist area, which can improve comfort for the wearer and reduce red marking. The carrier of the laminate wrapped around the edge of the chassis can provide strength to that portion of the chassis especially in embodiments in which the material at the longitudinal edges of the chassis is very thin. Furthermore, since the absorbent article according to the present disclosure and/or made according to the method disclosed herein does not have fastening tabs that are typically folded over and need to be opened by the wearer before use, the absorbent articles are easy to open and fasten around the body.

Also, the method of making an absorbent article according to the present disclosure has advantages over a method in which a fastening patch is directly attached to the diaper chassis, for example, on the topsheet side. During the manufacturing of absorbent articles, a web of a plurality of diaper chassis is usually held under tension. If a fastening patch were attached to the web with the web under tension, the fastening patch could curl when the web of diaper chassis is cut and the tension is released. In the method according to the present disclose, the carrier on both sides of the chassis can prevent such curling. Furthermore, direct placement of a fastening patch on the topsheet would require reconfiguration of equipment on a manufacturing line since the fastening patch would be applied from the topsheet side and not from the backsheet side. In the method according to the present disclosure, the laminate could still be applied to the backsheet side like in current manufacturing processes and then wrapped around the edge of the chassis.

SOME EMBODIMENTS OF THE DISCLOSURE

In a first embodiment, the present disclosure provides an absorbent article comprising:

a chassis with a topsheet side, a backsheet side, and first and second opposing longitudinal edges extending from a rear waist region to an opposing front waist region; and a laminate comprising a carrier having a first face and a second face and a fastening patch on a portion of the first face of the carrier, wherein the laminate is wrapped around the first longitudinal edge of the chassis in the rear waist region so that the second face of the carrier contacts the topsheet side and the backsheet side of the chassis, and wherein the fastening patch comprises fastening elements that are exposed on the topsheet side of the chassis.

In a second embodiment, the present disclosure provides the absorbent article of the first embodiment, wherein the second face of the carrier is attached to the chassis with adhesive.

In a third embodiment, the present disclosure provides the absorbent article of the first or second embodiment, wherein the second face of the carrier is non-adhesively bonded to the chassis.

In a fourth embodiment, the present disclosure provides the absorbent article of any one of the first to third embodiments, wherein the carrier comprises a nonwoven.

In a fifth embodiment, the present disclosure provides the absorbent article of any one of the first to fourth embodiments, wherein the fastening patch includes openings.

In a sixth embodiment, the present disclosure provides the absorbent article of any one of the first to fifth embodiments, wherein the fastening patch includes diamond- or hexagonal-shaped openings.

In a seventh embodiment, the present disclosure provides the absorbent article of any one of the first to fourth embodiments, wherein the fastening patch comprises at least one slit therethrough, wherein the slit is interrupted by an unslit bridging region in the fastening patch.

In an eighth embodiment, the present disclosure provides the absorbent article of any one of the first to seventh embodiments, wherein the laminate comprises a second fastening patch on a second portion of the first face of the carrier.

In a ninth embodiment, the present disclosure provides the absorbent article any one of the first to eighth embodiments, wherein the carrier has a length in a range from 50 millimeters to 80 millimeters and a width in a range from 15 millimeters to 40 millimeters.

In a tenth embodiment, the present disclosure provides the absorbent article of any one of the first to ninth embodiments, wherein there are two of the laminates wrapped around the first longitudinal edge of the chassis in the rear waist region.

In an eleventh embodiment, the present disclosure provides the absorbent article of the tenth embodiment, wherein there are two of the laminates wrapped around the second longitudinal edge of the chassis in the rear waist region.

In a twelfth embodiment, the present disclosure provides the absorbent article of any one of the first to eleventh embodiments, wherein the absorbent article is an adult incontinence article.

In a thirteenth embodiment, the present disclosure provides the absorbent article of any one of the first to twelfth embodiments, wherein a fold formed in the carrier where the laminate is wrapped around the first longitudinal edge of the chassis is flush with the first longitudinal edge.

In a fourteenth embodiment, the present disclosure provides the absorbent article of any one of the first to thirteenth embodiments, wherein the fastening patch does not extend beyond the first longitudinal edge of the chassis.

In a fifteenth embodiment, the present disclosure provides the absorbent article of any one of the first to thirteenth embodiments, wherein the fastening patch extends beyond the first longitudinal edge of the chassis.

In a sixteenth embodiment, the present disclosure provides a method of making an absorbent article, the method comprising:

providing a chassis having a topsheet side, a backsheet side, and first and second opposing longitudinal edges extending from a rear waist region to an opposing front waist region;

providing a laminate comprising a carrier having a first face and a second face and a fastening patch on a portion of the first face of the carrier;

wrapping the laminate around the first longitudinal edge of the chassis in the rear waist region so that the second face of the carrier contacts the topsheet side and the backsheet side of the chassis with the fastening patch positioned so that it does not extend beyond the first longitudinal edge of the chassis and so that fastening elements are exposed on the topsheet side of the chassis; and attaching the laminate to the chassis.

In a seventeenth embodiment, the present disclosure provides the method of the sixteenth embodiment, wherein the laminate is provided from a roll of a carrier web having a first face and a second face and a fastening strip on the first face of the carrier web.

In an eighteenth embodiment, the present disclosure provides the method of the seventeenth embodiment, further comprising slitting the roll to provide a plurality of the laminates.

In a nineteenth embodiment, the present disclosure provides the method of the seventeenth embodiment, wherein the roll includes lines of weakness through the carrier web and the fastening strip, wherein the lines of weakness connect a plurality of the laminates together.

In a twentieth embodiment, the present disclosure provides the method of the seventeenth embodiment, wherein the fastening strip is provided in a central portion of the carrier web such that the first face of the carrier web is exposed on each side of the fastening strip.

In a twenty-first embodiment, the present disclosure provides the method of the twentieth embodiment, further comprising slitting the roll through the central portion and in the cross-direction to provide a plurality of the laminates.

In a twenty-second embodiment, the present disclosure provides the method of the twentieth embodiment, wherein the roll includes lines of weakness through the carrier web and the fastening strip in the central portion and in the cross-direction, wherein the lines of weakness connect a plurality of the laminates together.

In a twenty-third embodiment, the present disclosure provides the method of any one of the seventeenth to twenty-second embodiments, wherein the roll is a planetary wound roll.

In a twenty-fourth embodiment, the present disclosure provides the method of any one of the seventeenth to twenty-second embodiments, wherein the roll is a level wound roll.

In a twenty-fifth embodiment, the present disclosure provides the method of any one of the seventeenth to twenty-fourth embodiments, wherein the fastening strip includes a pattern of openings.

In a twenty-sixth embodiment, the present disclosure provides the method of the twenty-fifth embodiment, wherein the openings are diamond- or hexagonal-shaped openings.

In a twenty-seventh embodiment, the present disclosure provides the method of any one of the seventeenth to twenty-fourth embodiments, wherein the fastening strip comprises at least one slit therethrough, where in the slit is interrupted by unslit bridging regions in the fastening strip to leave the fastening strip intact.

In a twenty-eighth embodiment, the present disclosure provides the method of any one of the seventeenth to twenty-seventh embodiments, wherein the roll comprises a second fastening strip on the first face of the carrier web.

In a twenty-ninth embodiment, the present disclosure provides the method of any one of the sixteenth to twenty-eighth embodiments, wherein attaching comprises adhesively bonding the second face of the carrier to the chassis.

In a thirtieth embodiment, the present disclosure provides the method of any one of the sixteenth to twenty-ninth embodiments, wherein attaching comprises non-adhesively bonding the second face of the carrier to the chassis.

In a thirty-first embodiment, the present disclosure provides the method of any one of the sixteenth to thirtieth embodiments, wherein the carrier web comprises a nonwoven.

In a thirty-second embodiment, the present disclosure provides the method of any one of the sixteenth to thirty-first embodiments, further comprising wrapping a second laminate around the first longitudinal edge of the chassis in the rear waist region and attaching the second laminate to the chassis.

In a thirty-third embodiment, the present disclosure provides the method of the thirty-second embodiment, further comprising wrapping third and fourth laminates around the second longitudinal edge of the chassis in the rear waist region and attaching the third and fourth laminates to the chassis.

In a thirty-fourth embodiment, the present disclosure provides the method of any one of the sixteenth to thirty-third embodiments, wherein the absorbent article is an adult incontinence article.

In a thirty-fifth embodiment, the present disclosure provides the method of any one of the sixteenth to thirty-fourth embodiments, wherein a fold formed in the carrier where the laminate is wrapped around the first longitudinal edge of the chassis is flush with the first longitudinal edge.

In a thirty-sixth embodiment, the present disclosure provides the method of any one of the sixteenth to thirty-fifth embodiments, wherein the fastening patch does not extend beyond the first longitudinal edge of the chassis.

In a thirty-seventh embodiment, the present disclosure provides the method of any one of the sixteenth to thirty-fifth embodiments, wherein the fastening patch extends beyond the first longitudinal edge of the chassis.

Various modifications and alterations of this disclosure may be made by those skilled the art without departing from the scope and spirit of the disclosure, and it should be understood that this invention is not to be unduly limited to the illustrative embodiments set forth herein. All patents and patent applications cited above are hereby incorporated by reference into this document in their entirety.

What is claimed is:

1. An absorbent article comprising:
    a chassis with a topsheet side, a backsheet side, and first and second opposing longitudinal edges extending from a rear waist region to an opposing front waist region; and
    a laminate comprising:
        a carrier having a first face and a second face opposite the first face; and
        a fastening patch on a portion of the first face of the carrier,
    wherein the laminate is wrapped around the first longitudinal edge of the chassis in the rear waist region so that the second face of the carrier or adhesive thereon contacts the chassis on the topsheet side and the backsheet side, wherein a fold formed in the carrier where the laminate is wrapped around the first longitudinal edge of the chassis is flush with the first longitudinal edge of the chassis or within five millimeters of the first longitudinal edge of the chassis, wherein the fastening patch does not extend beyond the first longitudinal edge of the chassis, and wherein the fastening patch comprises fastening elements that are exposed on the topsheet side of the chassis.

2. The absorbent article of claim 1, wherein the absorbent article is an adult incontinence article.

3. The absorbent article of claim 1, wherein the carrier comprises a nonwoven.

4. The absorbent article of claim 1, wherein the fastening patch includes diamond- or hexagonal-shaped openings, or wherein the fastening patch comprises at least one slit therethrough, wherein the slit is interrupted by an unslit bridging region in the fastening patch.

5. The absorbent article of claim 1, wherein the laminate comprises a second fastening patch on a second portion of the first face of the carrier.

6. The absorbent article of claim 1, wherein there are two of the laminates wrapped around the first longitudinal edge of the chassis in the rear waist region and two of the laminates wrapped around the second longitudinal edge of the chassis in the rear waist region.

7. The absorbent article of claim 1, wherein the second face of the carrier is attached to the chassis with adhesive.

8. The absorbent article of claim 1, wherein the second face of the carrier is non-adhesively bonded to the chassis.

9. A method of making the absorbent article of claim 1, the method comprising:
    providing the chassis having the topsheet side, the backsheet side, and the first and second opposing longitudinal edges extending from the rear waist region to the opposing front waist region;
    providing the laminate comprising:
        the carrier having the first face and the second face opposite the first face; and
        the fastening patch on the portion of the first face of the carrier;
    wrapping the laminate around the first longitudinal edge of the chassis in the rear waist region so that the second face of the carrier or the adhesive thereon contacts the chassis on the topsheet side and the backsheet side with the fastening patch positioned so that the fastening elements are exposed on the topsheet side of the chassis, wherein the fold formed in the carrier where the laminate is wrapped around the first longitudinal edge of the chassis is flush with the first longitudinal edge of the chassis or within five millimeters of the first longitudinal edge of the chassis, and wherein the fastening patch does not extend beyond the first longitudinal edge of the chassis; and attaching the laminate to the chassis.

10. The method of claim 9, wherein the laminate is provided from a roll of a carrier web having a first face and a second face and a fastening strip on the first face of the carrier web.

11. The method of claim 10, wherein the fastening strip is provided in a central portion of the carrier web such that the first face of the carrier web is exposed on each side of the fastening strip.

12. The method of claim 10, further comprising slitting the roll to provide a plurality of the laminates.

13. The method of claim 10, wherein the roll includes lines of weakness through the carrier web and the fastening strip, wherein the lines of weakness connect a plurality of the laminates together.

14. The method of claim 10, wherein the roll is a planetary wound roll or a level wound roll.

15. The method of claim 9, wherein attaching comprises adhesively bonding the second face of the carrier to the chassis.

16. The method of claim 9, wherein attaching comprises non-adhesively bonding the second face of the carrier to the chassis.

17. The method of claim 9, further comprising wrapping a second laminate around the first longitudinal edge of the chassis in the rear waist region, wrapping a third and fourth of the laminates around the second longitudinal edge of the chassis in the rear waist region, and attaching the second, third, and fourth laminates to the chassis.

* * * * *